US006793642B2

United States Patent
Connelly et al.

(10) Patent No.: US 6,793,642 B2
(45) Date of Patent: *Sep. 21, 2004

(54) FLOW CYTOMETER

(75) Inventors: Patrick R. Connelly, Rochester, NY (US); Stuart G. MacDonald, Pultneyville, NY (US); Robert W. Gray, Rochester, NY (US); Carol Gebert, Cambridge, MA (US)

(73) Assignee: Biomed Solutions, LLC, West Henrietta, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/918,076

(22) Filed: Jul. 30, 2001

(65) Prior Publication Data

US 2003/0036718 A1 Feb. 20, 2003

Related U.S. Application Data (63) Continuation-in-part of application No. 09/852,876, filed on May 10, 2001, and a continuation-in-part of application No. 09/850,250, filed on May 7, 2001.

(51) Int. Cl.[7] .................... A61M 37/00; A61M 1/36; G01N 33/48
(52) U.S. Cl. ............... 604/5.01; 604/6.1; 604/6.15; 604/4.01; 422/44; 436/63
(58) Field of Search .................. 604/4.01, 5.01, 604/5.02, 5.04, 6.08, 6.09, 6.11, 265; 210/668, 669; 422/82.09; 600/309, 310, 342, 407, 473, 476; 356/335–338; 435/4, 238.1; 424/489; 436/518

(56) References Cited

U.S. PATENT DOCUMENTS

| | | | |
|---|---|---|---|
| 3,910,256 A | * 10/1975 | Clark et al. | 600/325 |
| 4,915,683 A | * 4/1990 | Sieber | 604/5.02 |
| 5,057,413 A | 10/1991 | Terstappen et al. | |
| 5,188,633 A | * 2/1993 | Kratzer et al. | 606/12 |
| 5,444,527 A | 8/1995 | Kosaka et al. | |
| 5,703,959 A | 12/1997 | Asano et al. | |
| 5,804,143 A | * 9/1998 | Leary et al. | 422/73 |
| 5,907,240 A | 5/1999 | Carver, Jr. et al. | |
| 6,097,485 A | 8/2000 | Lievan | |
| 6,119,031 A | * 9/2000 | Crowley | 600/407 |
| 6,142,146 A | * 11/2000 | Abrams et al. | 128/203.15 |
| 6,193,681 B1 | * 2/2001 | Davidner et al. | 604/6.08 |
| 6,197,593 B1 | * 3/2001 | Deka et al. | 436/63 |
| 6,228,652 B1 | * 5/2001 | Rodriguez et al. | 436/63 |
| 6,281,018 B1 | 8/2001 | Kirouac et al. | |

* cited by examiner

*Primary Examiner*—Angela D. Sykes
*Assistant Examiner*—Leslie R. Deak
(74) *Attorney, Agent, or Firm*—Howard J. Greenwald (57) ABSTRACT

A flow cytometer containg a device for sampling cellular material within a body, comprising. The flow cytometer is adapted to mark cells within bodily fluid with a marker to produce marked cells, to analyze the marked cells, to sort the cells within the bodily fluid to produce sorted cells, and to maintain the sorted cells cells in a viable state.

3 Claims, 10 Drawing Sheets

FLOW CYTOMETER

CROSS-REFERENCE TO RELATED PATENT APPLICATIONS

This application is a continuation-in-part of applicants' copending patent applications U.S. Ser. No. 09/852,876 (filed on May 10, 2001) and U.S. Ser. No. 09/850,250 (filed on May 7, 2001).

FIELD OF THE INVENTION

A flow cytometer adapted to both detect and treat mammalian cells, containing means for affixing a label to cellular material and thereafter removing such label.

BACKGROUND OF THE INVENTION

Flow cytometers are well known to those skilled in the art. By way of illustration and not limitation, one may refer to, e.g., U.S. Pat. Nos. 6,198,110, 6,197,744, 6,197,593, 6,197,540, 6,197,539, and the like.

Most of the prior art flow cytometers are relatively large and unwieldy and, thus, cannot readily accompany a patient in his everyday endeavors. Furthermore, most prior art flow cytometers are not adapted to sample cellular material directly; the analyte generally used with these prior art machines must be extracted and prepared in vitro from a cellular source.

It is an object of this invention to provide a flow cytometer which is portable, which can be affixed to the body of a patient, which can directly sample cellular material, and which can treat cellular material.

It is another object of this invention to provide a flow cytometer which can be used therapeutically as well as diagnostically.

SUMMARY OF THE INVENTION

In accordance with this invention, there is provided a flow cytometer which comprises means for sampling cellular material, a means for marking cells within said bodily fluid with a marker to produce marked cells, means for analyzing the cellular material, means for removing such marker from the marked cells, means for sorting the cellular material, means for modifying a portion of the cellular material, and means for maintaining a portion of the cellular material which has been analyzed in a viable state.

BRIEF DESCRIPTION OF THE DRAWINGS

The invention will be described by reference to the specification and to the following drawings, in which like numerals refer to like elements, and in which:

FIG. 3, consisting of FIGS. 3A, 3B, and 3C, schematically illustrate the actions of the pump of the assembly depicted in FIG. 2;

DESCRIPTION OF THE PREFERRED EMBODIMENTS

Figure 1:
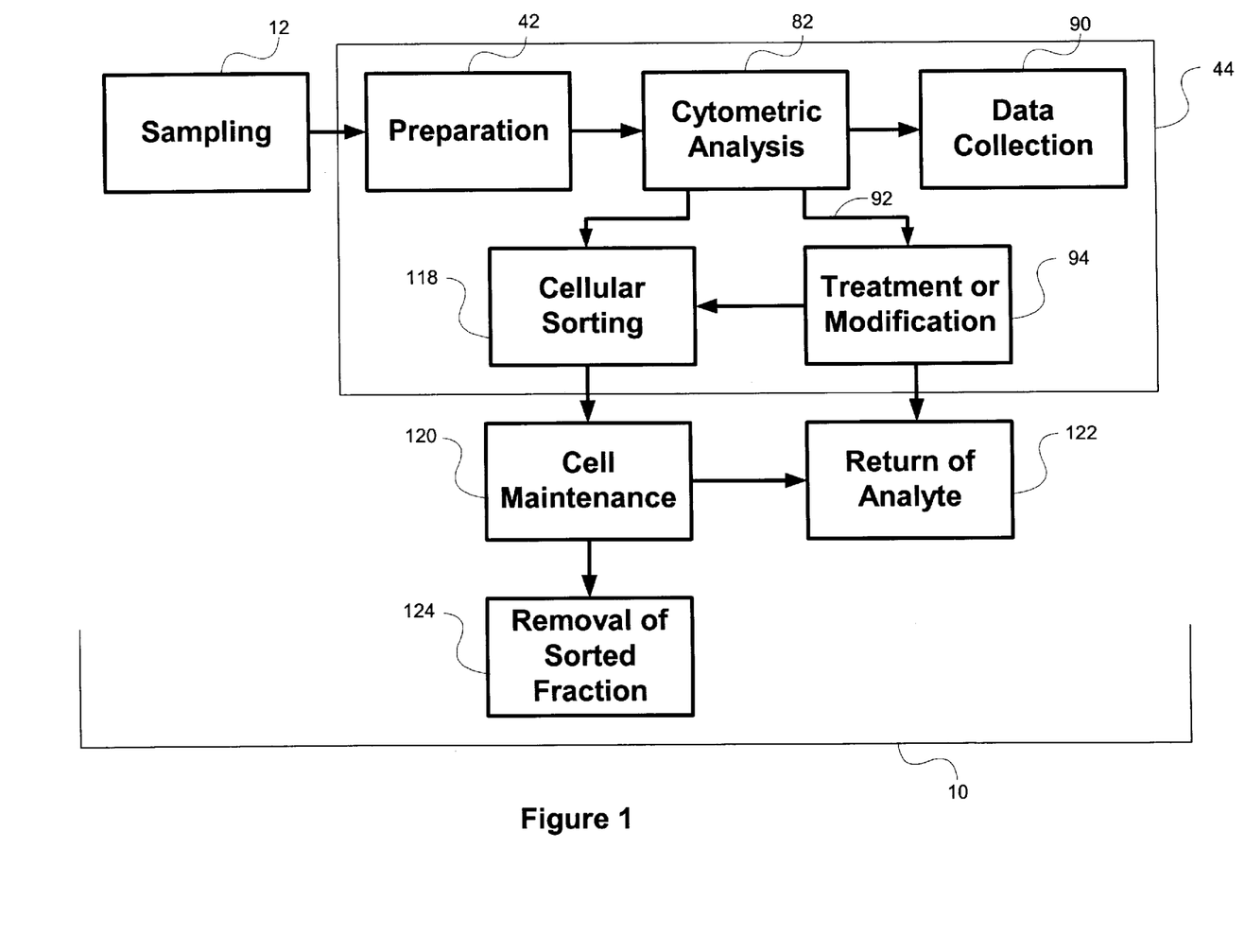
FIG. 1 is a flow diagram of one preferred process of the invention.

FIG. 1 is a flow diagram of one preferred process 10 for analyzing, treating, and maintaining certain bodily fluids.

Sampling

In step 12 of the process, the bodily fluids are sampled. One may use any conventional means for sampling the body fluids. The body fluids which are typically sampled include, e.g., blood, lymph, spinal fluid, bone marrow, and the like.

In one embodiment, the body fluids are sampled by means of the sampling system described in U.S. Pat. No. 6,159,164, the entire disclosure of which is hereby incorporated by reference into this specification. The system of this patent samples a body fluid through a tube attached to a patient's body; and the system is operable buy a user having a hand, including a palm, a thumb, and at least a first finger and a second finger. The system comprises a fluid sampling site connected to the tube; means for receiving the tube; means for forming a chamber; means for selectively increasing the size of the chamber to a maximum volume and for decreasing the size of the chamber to a minimum volume, the means for increasing and decreasing the size of the chamber being operable by moving the first and second fingers or the thumb in a flexion movement toward the palm to achieve the maximum volume of the chamber, the means for increasing and decreasing the size of the chamber also being operable by moving the first and second fingers or the thumb in a flexion movement toward the palm to achieve the minimum volume of the chamber such that the same motion of the user's first and second fingers can selectively accomplish the maximum volume to aspirate fluid from the patient's body to the fluid sampling site or accomplish the minimum volume to expel the fluid into the patient's body.

Figure 2:
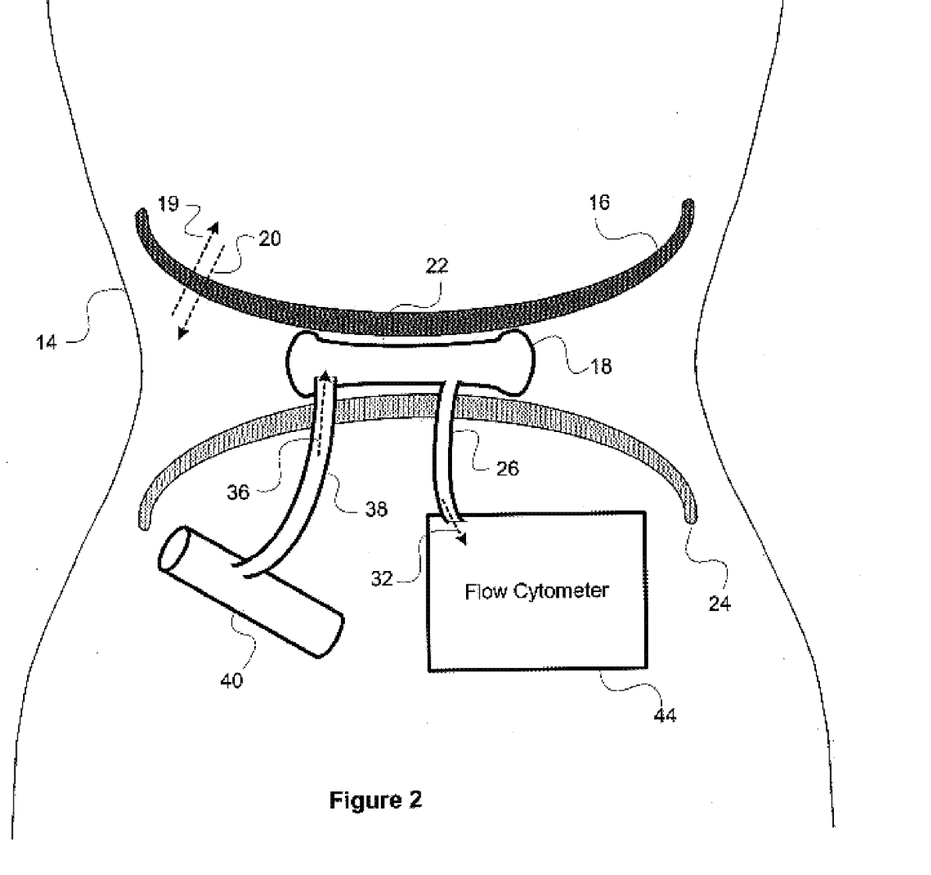
FIG. 2 is a schematic of one preferred assembly of the invention for sampling, wherein the assembly is comprised of a flow cytometer.

FIGS. 2 and 3 indicate another sampling assembly which may be used. FIG. 2 outlines the pump's bodily location and FIG. 3 details the pumping action. Referring to FIGS. 2 and 3, a patient has disposed within her body, beneath her diaphragm 16, a pump 18 which is actuated by the movement of diaphragm 16 in the direction of arrows 19 and 20.

Referring to FIG. 3, the pump 18 has a deformable and elastic casing 22. When casing 22 is compressed between diaphragm 16 and abdominal wall 24, its interior volume will decrease, and fluid disposed within pump 18 will be discharged through line 26 to flow cytometer 44.

The pump 18 comprises one way flow valve 30, which allows flow only in the direction of arrow 32; and it also comprises one way flow valve 34, which only allows flow in the direction of arrow 36. Thus, when casing 22 is compressed, fluid only may flow through line 26; when the compressed casing 22 is allowed to expand to its original shape (when the diaphragm 16 relaxes), the fluid may flow only through line 38.

Although the pump 18 is shown disposed beneath the patient's diaphragm 16, it will be apparent that such pump 18 may be disposed beneath or nearby other parts of a body which expand and contract. Thus, by way of illustration and not limitation, the pump 18 may be positioned between lung and ribcage, between muscle and bone, between a heart and a sternum, and the like.

Referring again to FIG. 2, it will be apparent that, every time the diaphragm 16 expands and thereafter contracts, fluid will be withdrawn from blood vessel via line 38 into pump 18; and the fluid within such pump 18 will be fed to flow cytometer 44 via line 26 upon the next expansion of the diaphragm 16. This is one preferred means of sampling the blood in blood vessel 40, and it operates continuously with the movement of diaphragm 16.

Figure 3A:
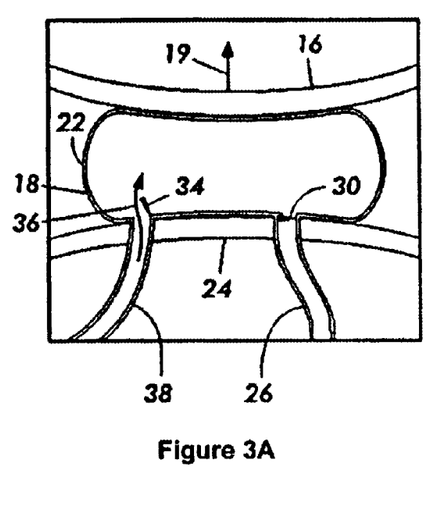
Figure 3B:
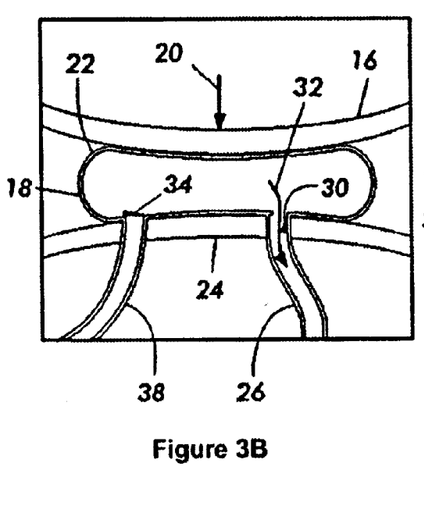
Figure 3C:
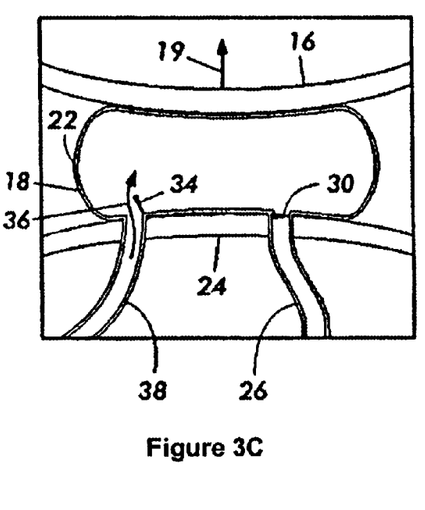

FIGS. 3A, 3B, and 3C illustrate the operation of pump 18 in its intake phase (FIG. 3A), its expulsion phase (FIG. 3B), and its subsequent intake phase (FIG. 3C). The pump 18 is compressed when the diaphragm 16 moves in the direction of arrow 20; and it is allowed to return to its non-compressed state when the diaphragm 16 moves in the direction of arrow 19.

In another embodiment, not shown, the pump 18 is replaced by a piezoelectric or electrostrictive assembly (not shown) which, upon pressure being applied to it, produces a difference of potential sufficient to actuate a pump to which it is electrically connected.

Sample Preparation

Referring again to FIG. 1, in step 42 of the process, the bodily fluid which has been sampled is then prepared for analysis. One may use any method for enumerating and distinguishing between fluid cell populations in a bodily sample. Thus, by way of illustration and not limitation, one may use the method described in U.S. Pat. No. 6,197,593, the entire disclosure of which is hereby incorporated by reference into this specificaiton.

In the first step of the process of U.S. Pat. No. 6,197,593, a biological sample is contacted with two or more blood cell populations with a selective nucleic acid specific blocking agent to form a sample mixture. The sample mixture is then contacted with a cell membrane permeant, red-excited dye without significantly disrupting cellular integrity of the cells to form a dyed sample mixture. The dyed sample mixture is excited with light in a single red wavelength; and, thereafter, fluorescence emitted from different cell populations in the dyed sample mixture are measured, wherein the fluorescence emitted from one blood cell population is distinguishable from the fluorescence emitted from another blood cell population.

Figure 4:
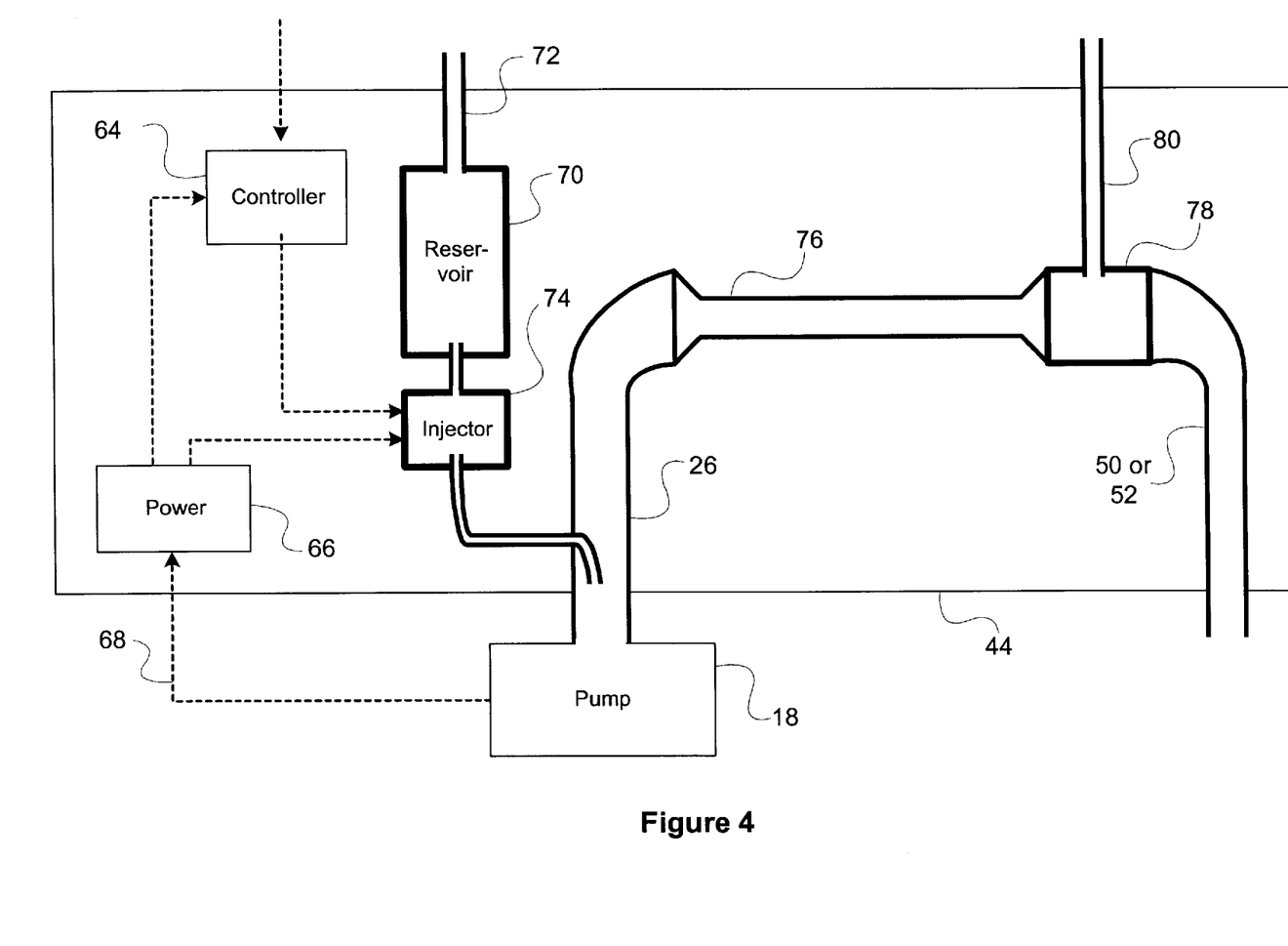
FIG. 4 is a schematic diagram of one preferred means for preparing a bodily fluid for analysis.

Referring to FIG. 4, the appropriate dye(s) or other markers are fed to reservoir 70 by line 72 and, in response to one or more signals from controller 64, is fed into injector 74 and thence into line 26, where the dye(s) mix with the fluid disposed within such line 26 and selectively mark them.

After the marked bodily fluid has been analyzed and, optionally, treated, and prior to the time it is returned via line 50 or 52 to either the body or to a reservoir, the marker (dye) may be removed from the fluid by conventional means. Thus, by way of illustration and not limitation, the marker may be removed by means of an adsorption column 78 and/or by other adsorption means. Thus, e.g., the dye may be removed by other means, including chemical means. By way of illustration and not limitation, processes for stripping dyes or decolorizing various materials are known in the art. For example, U.S. Pat. No. 4,227,881 discloses a process for stripping dyes from textile fabric which includes heating an aqueous solution of an ammonium salt, a sulfite salt and an organic sulfonate to at least 140.degree. F. (60.degree. C.) and adding the dyed fabric to the heated solution while maintaining the temperature of the solution. U.S. Pat. No. 4,783,193 discloses a process for stripping color from synthetic polymer products by contacting the colored polymer with a chemical system.

It will be apparent that one can use one of several different physical and/or chemical means of removing the dye/marker from the bodily fluid; the aforementioned description is illustrative and not limitative. Regardless of which means are used, a purified bodily fluid is returned via line 50/52 to either the body or a reservoir.

During the purification process, additional material needed for such process may be charged via line 80, and/or dye and/or other waste material may be removed via line 80.

Referring again to FIG. 4, the reservoir 70 may contain one or more markers, and/or it may contain diluent to preferably dilute the bodily fluids so that preferably only one cell passes by any particular point in flow chamber 76 at any one time. As will be apparent, this "laminar flow condition" facilitates the analyses of the bodily fluid by optical means.

Analysis

Referring again to FIG. 4, the selectively marked bodily fluid(s) are then funneled into the flow chamber 76 of the cytometer 44, wherein they are subjected to analysis by conventional optical means. Referring again to FIG. 1, in step 82 of the process the marked bodily fluid is analyzed. One may conduct, e.g., flow cytometeric analyses in accordance with the procedures described in the patents listed elsewhere in this specification; and one may use the devices disclosed in such patents for such analyses.

Figure 5:
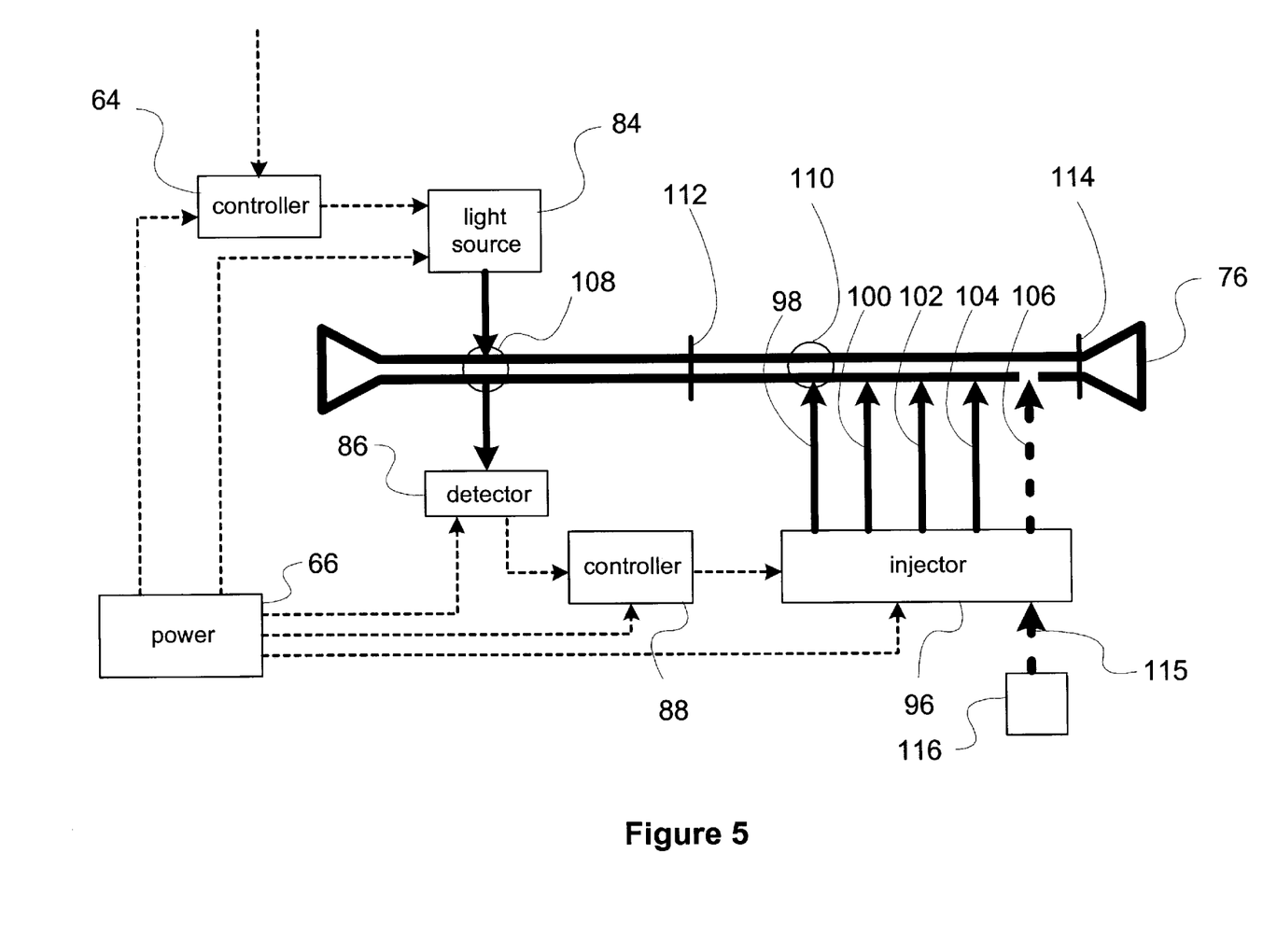
FIG. 5 is a schematic of the detection/treatment system of the flow cytometer.

One such analytical device is illustrated schematically in FIG. 5. For the sake of simplicity of representation, unnecessary detail has been omitted from FIG. 5. Referring to FIG. 5, and in the embodiment depicted therein, a light source 84 is caused to focus on flow chamber 76. The amount of light transmitted through flow chamber 76 will vary with the properties of the bodily fluid within such chamber; see, e.g., U.S. Pat. Nos. 6,197,756, 6,197,593, 6,197,583, 6,197,582, 6,197,568, 6,197,540, and the like. The entire disclosure of each of these United States patents is hereby incorporated by reference into this specification.

Data Collection

Referring to FIG. 5, the light transmitted through flow chamber 76 is detected by detector 86 which may, e.g., be a photodetector. Data is fed from detector 86 to controller 88.

Controller 88 is equipped with a database indicating the properties of normal bodily fluids. The property of any particular bodily fluid being analyzed can be compared with this database to determine whether they correlate. A lack of correlation may indicate a disease state, which can be thereafter treated by the cytometer 44.

Referring again to FIG. 1, in step 90 data is collected from the analysis conducted in controller 88. Historical data may also be fed to the data collection device, either before, during, or after the analysis 82 of the bodily fluid. The collection of data in step 90, and it use, may be done in accordance with U.S. Pat. No. 6,197,593, the entire disclosure of which is hereby incorporated by reference into this specification.

Data from data collection step 90 may be added to from external sources. Alternatively, data from data collection step 90 may be exported to one or more external devices.

In one embodiment, not shown, when analysis step 82 and data collection step 90 indicate the presence of a dangerous abnormal condition within the bodily fluid, an external alarm is activated to warn the patient. When analysis 82 of the bodily fluid indicates that it is abnormal, the bodily fluid may be charged via line 92 to treatment step 94. As is indicated in FIG. 5, this treatment step 94 may occur in line within the flow chamber 76.

Treatment

Referring again to FIG. 5, injector 96 is operatively connected to both detector 86 and controller 88 and, in response to signals therefrom, feeds energy and/or material to the bodily fluid to treat it.

One may feed radiation 98 to the bodily fluid to treat it. Thus, e.g., one may cause ultraviolet radiation to impact flow chamber 76 and to kill cancerous cell(s) disposed within such flow chamber 76. Thus, e.g., one may use electrical discharge 100 by means such as, e.g., electroporation. Thus, e.g., one may use magnetic fields 102. Thus, e.g., one may use sound particles and rays 104. Alternatively, or additionally, one may feed material via line 106 into flow chamber 76 which is adapted to kill or modify the abnormal cell(s).

One may use any of the materials commonly used to kill or modify cells. Thus, by way of illustration and not limitation, one may use gene vectors, viral particles, antibodies, chemotherapeutic agents, etc. Thus, e.g., one may do selective gene therapy on any particular cell.

To the extent, if any, there is a need to replenish material within injector 96, such material may be fed to injector 96 via line 115 from reservoir 116.

When it is desired to cause a particular cell to remain at a particular location for any period of time, the controller 64 can cause the close valves 112 and 114 so that fluid disposed between such valves cannot flow.

Because the flow cytometer 44 is capable of detecting one cell at a time, any abnormal cell detected at point 108 may be treated at point 110, e.g., the controller 88 determining precisely where such particular cell is at any point in time.

Return

Figure 6:
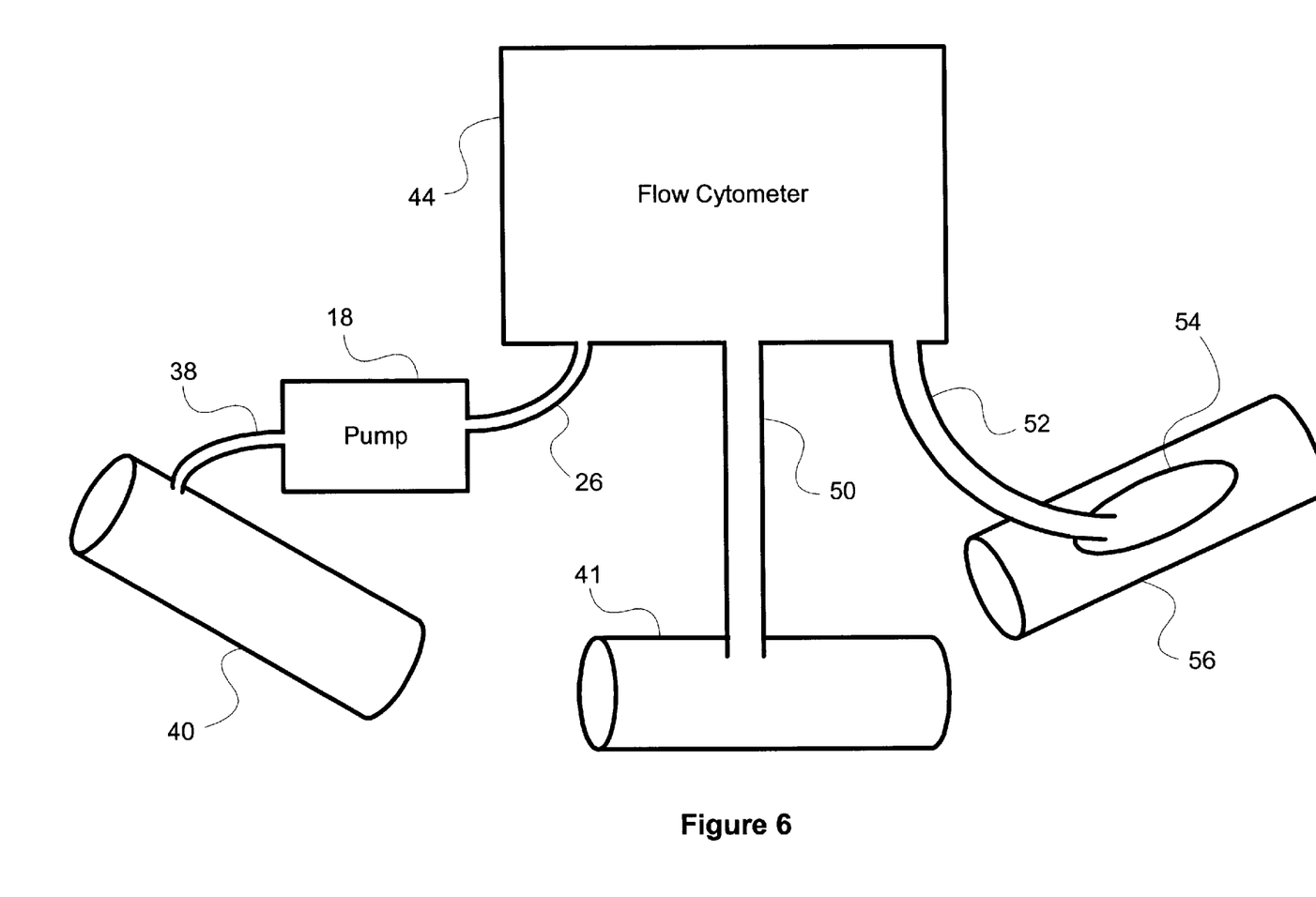
FIG. 6 is a schematic of the flow cytometer assembly in relation to the location of bodily fluids.

As is illustrated in FIG. 1, and in step 122, the cells or bodily fluid treated in step 94 may be returned to the body in step 122. In the preferred embodiment depicted in FIG. 6, body fluids which have been analyzed by cytometer 44 may be fed via line 50 to vessel 41, which may be the same or different from the blood vessel 40, from which the bodily fluid was sampled. Alternatively, or additionally, such analyzed bodily fluids may be fed via line 52 to reservoir 54 which, in the embodiment depicted, is disposed in a blood vessel 56.

Sorting

Referring again to FIG. 1, the cells analyzed in step 82 may be sorted in sorting step 118 according to criteria detected by the detector 86 and analyzed by controller 88. In this sorting step, one may selectively segregate and collect certain cells within the bodily fluid. One may use conventional flow cytometer sorters in this step; see, e.g., U.S. Pat. Nos. 5,985,216 and 5,998,212, the entire disclosure of each of which is hereby incorporated by reference into this specification.

In one embodiment, stem cells are sorted from the bodily fluid. The identification and separation of such stem cells may be conducted by conventional means such as, e.g., the means disclosed in U.S. Pat. No. 5,665,557, the entire disclosure of which is hereby incorporated by reference into this specification. In the process of this patent, for epitope mapping studies, quintuplicate aliquots of KG1a cells (0.5_ 1.times.10.sup.6/analysis) were incubated for 30 min on ice with either 5 ul 8A3, 7D1, 7C5 or 8A1. 2 ul biotinylated conjugates of 8A3, 7D1, 7C5 or 8A1 were then added to each of the 4 sets of the above samples (i.e. 16 samples total for this experiment) for a further 30 min on ice. Cells were then washed twice in cold phosphate buffered saline by centrifugation and incubated with cychrome-conjugated streptavidin for a final 30 min on ice. Stained cells were then analyzed by flow cytometry using a FACScan (Becton Dickinson Instrument Systems (BDIS)

The stem cells sorted in step 118 may be collected and thereafter used for many different purposes.

Maintenance

Figure 7:
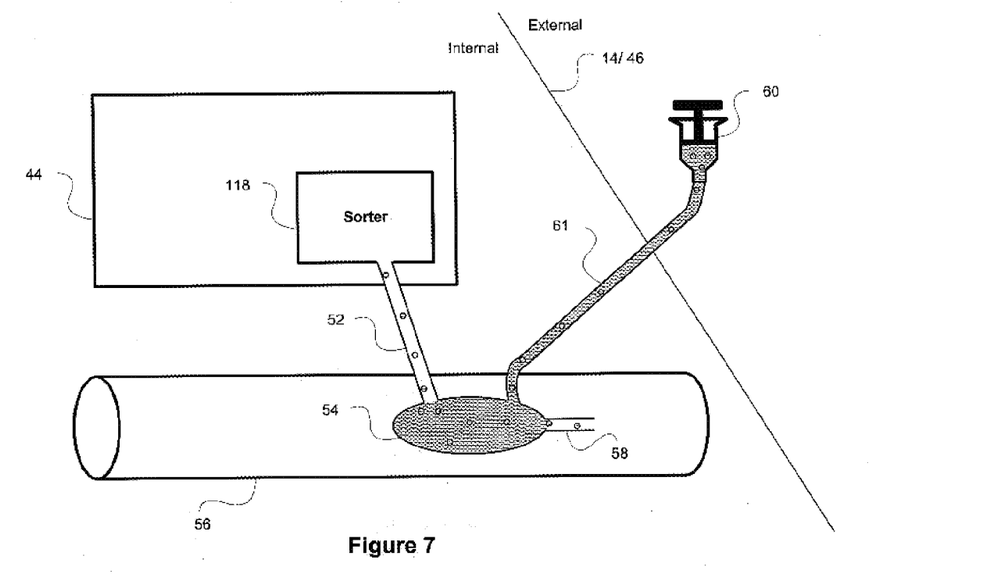
FIG. 7 is a schematic of one preferred means for maintaining a viable bodily fluid.

FIG. 7 is a schematic of a means for maintaining bodily fluid (and/or a portion thereof) in maintenance step 120. Referring to FIG. 7, some or all of the cells which have been sorted in sorter 118 may be passed via line 52 to reservoir 54. In one embodiment, not shown, sorter 118 is bypassed and bodily fluid is directly passed into reservoir 54.

In the embodiment depicted in FIG. 7, reservoir 54 is disposed within blood vessel 56, and which is composed of porous material. In another embodiment, not shown, reservoir 54 may be disposed adjacent to a blood vessel, and/or be disposed adjacent to the intestines. This allows all necessary nutrients and supplies to be available to the retained cells. It also allows for waste products to be removed from reservoir 54. The porous material has a pore size that allows cells to remain within reservoir 54, but which allows nutrients and waste products to diffuse freely.

Removal

Referring to FIG. 7, one may remove some or all of the sorted material in step 122 and maintained in reservoir 54 by means, e.g., of syringe 60 and line 61. One may also withdraw fluid from reservoir 54 into blood vessel 56 by means of line 58.

Location

Figure 8:
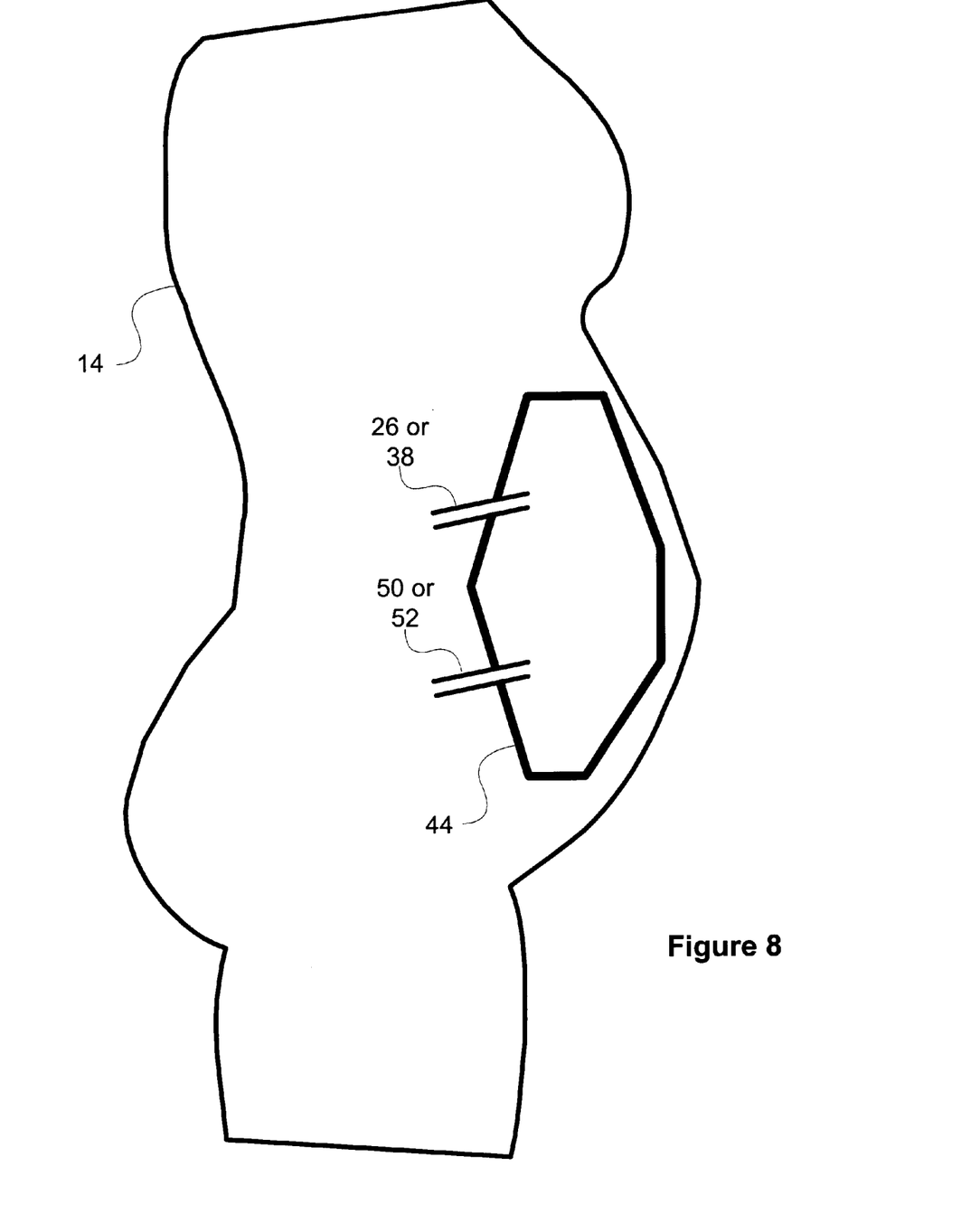
FIG. 8 is a schematic of a flow cytometer disposed within a living body.

The flow cytometer 44 may be disposed either within or without the patient's body. Referring to FIG. 8, and in the preferred embodiment depicted therein, it will be seen that a flow cytometer 44 is disposed in a patient's body. In the embodiment depicted in FIG. 8, the flow cytometer 44 is disposed beneath a patient's skin, in the abdominal cavity. The flow cytometer 44 may be implanted within the patient's body by conventional means. Thus, by way of illustration and not limitation, one may implant flow cytometer 44 by the method disclosed in U.S. Pat. No. 6,198,950, the entire disclosure of which is hereby incorporated by reference into this specification. In the process of such patent, the implantable device is implanted under the skin in such a manner that the cannula projects into a blood vessel. Thus, by way of further illustration, one may use the implantation processes and/or techniques disclosed in U.S. Pat. Nos. 6,198,969, 6,198,971, 6,198,965, 6,198,952, and the like. The entire disclosure of each of these U.S. patents also is incorporated by reference into this specification.

Figure 9:
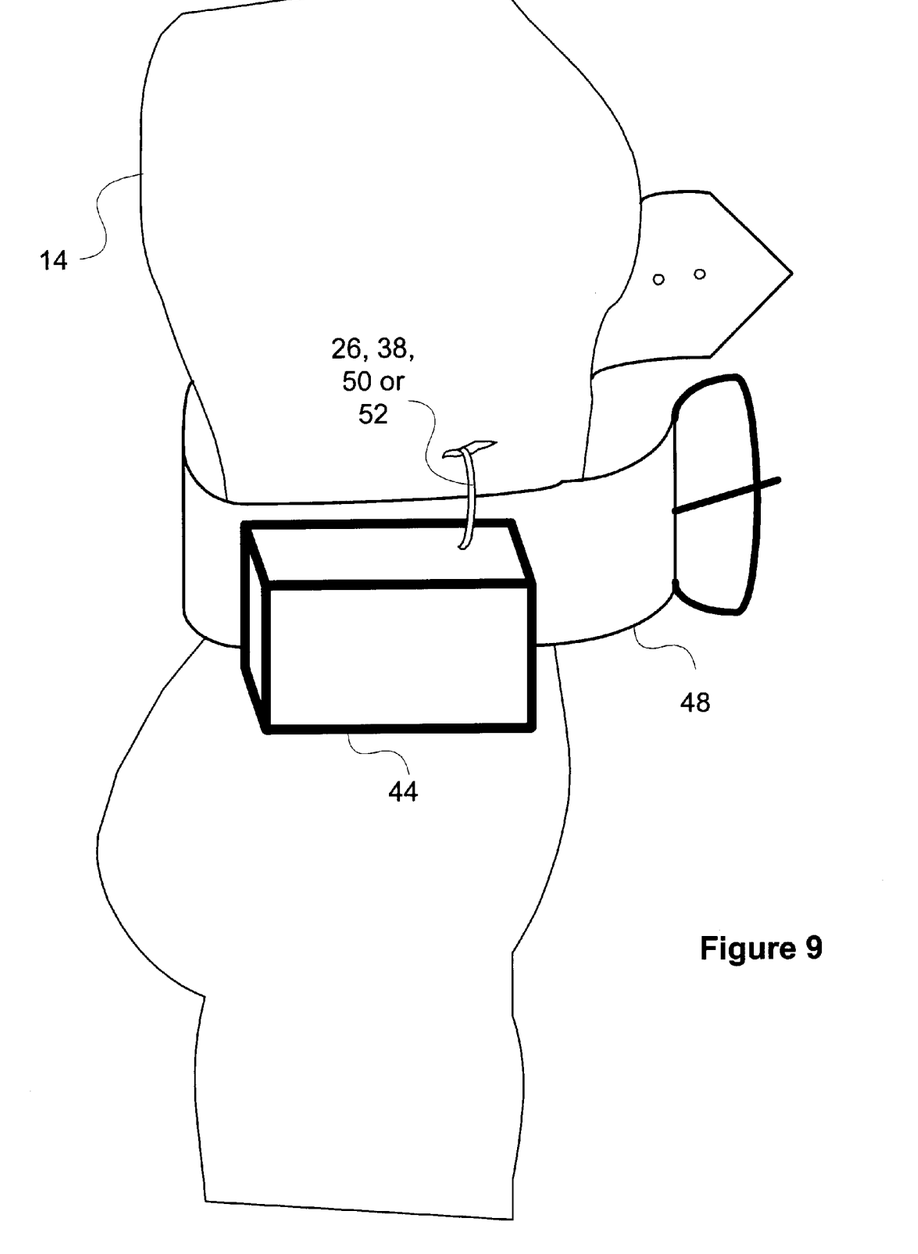
FIG. 9 is a schematic of a flow cytometer disposed outside of a living body.

In another embodiment, illustrated in FIG. 9, flow cytometer 44 is disposed outside the body 14 rather than inside it. In this embodiment, cytometer 44 may be removably attached to the body 14 by conventional means such as, e.g., belt 48 extending around the torso of the patient. The bodily fluid is sampled from, returned to or maintained in the body via cannulae tubes 26, 38, 50 or 52.

Size

The flow cytometer 44 preferably has a weight of less than 12 pounds and, more preferably, weighs less than about 6 pounds. In one embodiment, the flow cytometer 44 is made from miniaturized components and weighs less than about 3 pounds. Technologies that enable this size and weight to be achieved include low energy lasers and advanced flow chambers that allow cells to flow in a narrowly focused laminar flow stream.

Power

Referring to FIG. 5, the controller 64 is operatively connected to a power source 66. In one embodiment, depicted in FIG. 4, pump 18 provides power to power source 66. Thus, every output cycle of pump 18 provides some hydraulic pressure via line 68 to pump 66. This hydraulic pressure is converted into electrical power by conventional means such as, e.g., piezoelectric means.

In another embodiment, power source 66 is a battery. The battery may be rechargeable. Thus, in one aspect of this embodiment, the battery is recharged by electromagnetic radiation. The electromagnetic radiation may be transferred from a source disposed within the patient's body; or it may be transferred from a source external to the patient's body. Thus, e.g., an magnetic field may be produced by passing alternating current through a wire or coil, and this alternating magnetic field may be transmitted through a patient's skin into his body and coupled with an transducer, which produces alternating current from the alternating magnetic field.

In another embodiment, not shown, material and/or energy is fed to power source 66 via a line (not shown), and this material and/or energy is adapted to furnish power to power source 66. Thus, e.g., the material charged to power source 66 may undergo and/or facilitate a reaction which produces energy consumed by power source 66.

Materials

Referring to FIG. 3, in one embodiment, the casing 22, of pump 18 is made from a flexible, elastic biocompatible material. In embodiments where the flow cytometer is located subcutaneously, the flow cytometer is made from biocompatible materials such as surgical steel or encased in biocompatible materials. All cannulae and tube are preferably made from flexible, biocompatible materials. Flow chamber 76 is preferably transparent to the desired light source.

Bodily Fluids

In the preferred embodiment depicted in all figures, flow cytometer 44 is sampling blood. In another embodiment, not shown, the flow cytometer 44 is so disposed that it samples bodily liquids such as, e.g., lymph, bone marrow, spinal fluid, and the like. As will be apparent to those skilled in the art, the flow cytometer 44 is adapted to sample and analyze and treat unmodified bodily liquids, that is, bodily liquids occurring in their natural state within the body.

Another Preferred Process of the Invention

Figure 10:
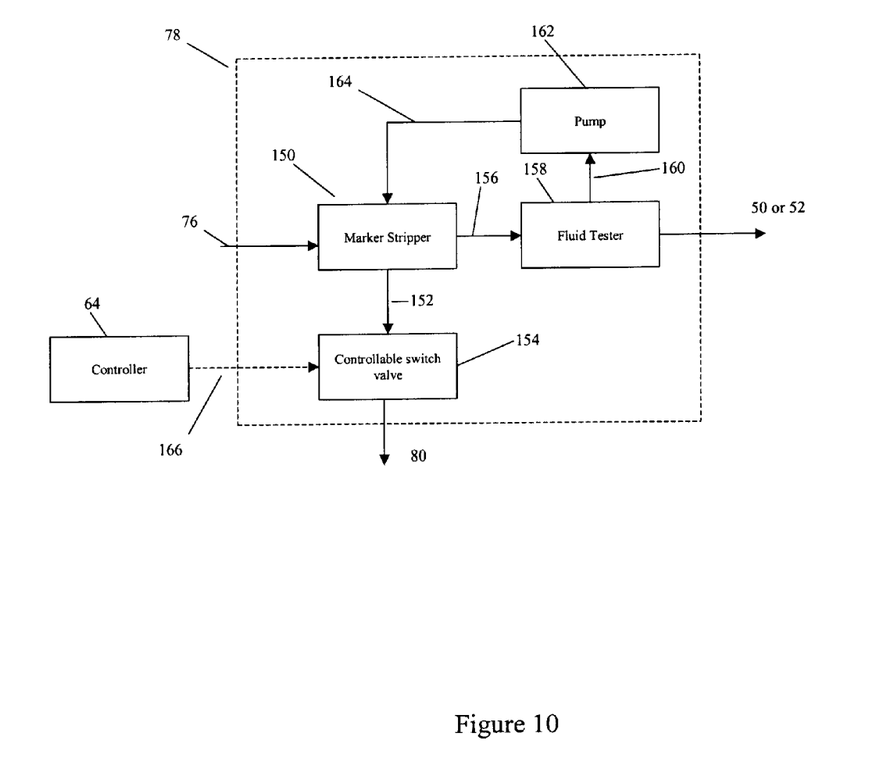
FIG. 10 is a block diagram of another preferred process of this invention.

FIG. 10 is a block diagram of a preferred process 161 which utilizes element 78 (see FIG. 4). In the first step of this process, the output of flow chamber 76 (see FIG. 4) flows to component 78 of FIG. 4 which comprises of marker/stripper 150 of FIG. 10, wherein the marker is removed from the cellular material flowing through chamber 76. As will be apparent, the marker had first been affixed to such cellular material with injector 74 (see FIG. 4); this marker is discussed elsewhere in this specification.

As is known to those skilled in the art, flow cytometry (FC) is used to detect variations in cell types and/or particles by use of fluorescent labeling and endogenous cellular optical properties. Originally flow cytometric systems were used solely to rapidly count cells. The cells were traditionally isolated from tissue or blood and labeled with fluorescent markers or antibodies conjugated with fluorescent tags. A variety of cell types have been analyzed using these methods. Cell volume and type could also be characterized by the intensity and frequency component of transmitted light. Following isolation, cells were then fed through a flow chamber of specified dimensions.

Optical flow cytometer systems are based on either the detection of intrinsic scattering properties of cells (which include the cellular membrane structure, organelle concentration and structure, cytoplasmic structure, and DNA/chromatin structure) and/or of detection of emitted light from fluorescently labeled cells. The cells are usually labeled with fluorescent conjugated antibodies to cell surface receptors or cytoplasmic proteins. A source for the emission of a specified frequency of energy (i.e., a light source) is directed toward the stream of flowing cells through a narrow flow cell. It is possible to detect with a photomultiplier tube array the scattering of light through the cell ("forward light scattering"), the scattered light which is reflected orthogonal to the direction of the flow ("side light scattering"), and the fluorescence emission from fluorescently conjugated antibodies to a variety of factors within and on the cell surface.

Referring again to FIG. 10, and in the embodiment depicted therein, a bodily fluid (not shown) is flowing in through chamber 76. In one embodiment, the bodily fluid is blood, and it is caused to flow by the action of a heart. In another embodiment, the bodily fluid may be a non-hematologic fluid such as, e.g., lymph, urine, cerebrospinal fluid, and the like. In another embodiment, the bodily fluid is comprised of red blood cells and/or leukocytes and/or neutrophils and/or other cells or cellular material. Each of these components will have a different optical response to a specified optical input.

The cells of the bodily fluid preferably have either endogenous optical properties, and/or they are labeled to provide optical properties. Thus, e.g., the cells may be labeled with flourescently-conjugated antibodies. Thus, e.g., in one embodiment the flow cytometer will utilize either injected fluorescent contrast or emitted light energies intrinsic to specific cells themselves. As is known to those skilled in the art, antibodies may be conjugated with polymeric dies with fluorescent emission moieties such as aminostyryl pyridinium (see, e.g., U.S. Pat. No. 5,994,143, the entire disclosure of which is hereby incorporated by reference into this specification).

As is apparent, and in one preferred embodiment, the function of a flow cytometry system is to determine which, if any, of four antigens are carried by blood cells, including cell CEL. To this end, respective antibodies for the antigens are derivatized with respective fluorochromes allophycocyanin (APC), peridinin chlorophyl protein (PerCP), fluorescein isothiocyanate (FITC), and R-phycoerythrin (RPE). Reference may be had, e.g., to U.S. Pat. No. 5,682,038 for "Fluorescent-particle analyzer with timing alignment for analog pulse subtraction of fluorescent pulses arising from different excitation locations," the entire disclosure of which is hereby incorporated by reference into this specification.

By way of further illustration, U.S. Pat. No. 5,994,143 ("Polymeric fluorophores enhanced by moieties providing a hydrophobic and conformationally restrictive microenvironment") discloses another process for fluorescent antibody conjugation; the entire disclosure of this U.S. patent is hereby incorporated by reference into this specification. In this patent, it is disclosed that the first of two closely positioned fluorophores may be excited by light of a given wavelength. Then, instead of emitting light of a longer wavelength, the excited fluorophore transfers energy to the second fluorophore. That transferred energy excites the second fluorophore, which then emits light of an even longer wavelength than would have been emitted by the first fluorophore. An example of such an energy transfer arrangement involves phycobiliprotein-cyanine dye conjugates. Subjecting these conjugates to an about 488 nm laser light excites the phycobiliprotein. The phycobiliprotein will then, without itself irradiating, transfer energy to the cyanine fluorophore at the excitation wavelength of the cyanine, which is coincident with the emission wavelength of the phycobiliprotein, about 580 nm. Consequently, the cyanine fluorophore is thereby excited and subsequently emits light of its emission wavelength of about 680 nm. This type of energy transfer system in often referred to as a "tandem energy transfer system."

In one embodiment, not shown, dyes may be injected in a manner similar to that used to inject contrast agents for medical ultrasound techniques. See, e.g., U.S. Pat. No. 6,177,062 ("Agents and methods for enhancing contrast in ultrasound imaging"), the entire disclosure of each of which is hereby incorporated by reference into this specification. The fluorescent dyes preferably are not toxic to the living body and care must be taken in preparation of the fluorescent dyes. The combination of different wavelength fluorochromes conjugated to antibodies to different cells along with the endogenous optical properties of the cells will provide a complex multiparameter data set where differing signals from different cells will be discernable.

When performing particle analysis in the body one may need to use fluorescent labels or other dyes which may be toxic to the body or to cells. In one embodiment, the bodily fluid is comprised of plasma. In one embodiment, the device 44 detects the intrinsic scattering properties of cells (which are influenced by the cellular membrane structure, organelle concentration and structure, cytoplasmic structure, and DNA/chromatin structure). Alternatively the following embodiment may be utilized.

Referring again to FIG. 10, and in the preferred embodiment depicted therein, the marker or markers are removed from the bodily fluid in marker/stripper 150. One may use conventional means from removing the marker(s) from the bodily fluid. Thus, by way of illustration and not limitation, the marker may be removed by means of an adsorption column (not shown) and/or by other adsorption means. Thus, e.g., the dye may be removed by other means, including chemical means. By way of illustration and not limitation, processes for stripping dyes or decolorizing various materials are known in the art. U.S. Pat. No. 4,783,193 discloses a process for stripping color from synthetic polymer products by contacting the colored polymer with a chemical system.

In one embodiment, dye separators are used in maker/stripper 150, and these dye separators may require additional plasma fluid which may be obtained from a plasma reservoir (not shown) which is connected to the dye separators.

After the marker/stripper 150 has removed the marker(s) or otherwise rendered the fluid harmless, the removed marker(s)/dye(s) are fed via line 152 to a controllable switch valve, which can feed the marker(s)/dye(s) to one or more different locations, depending upon the nature of the marker (s)/dye(s).

Thus, e.g., in one embodiment, the dyes are fed via line 80 to dye reservoir 70 (see FIG. 4). Thus, e.g., in another embodiment (not shown) another reservoir/holding tank (not shown), to be disposed of. In another embodiment, not shown, the dye(s)/marker(s) may be fed to the patient's bladder and/or gastrointestinal tract, depending upon the toxicity and/or degradability of the dye(s)/marker(s). The controller 64, which includes one or more suitable sensors (see FIG. 4), controls to which destination(s) the dye(s)/marker(s) are to be sent.

Referring again to FIG. 10, the purified body fluid is fed via line 156 to a fluid tester 158, which determines the degree of purity of the body fluid. If tester 158 determines that the body fluid is not purified enough, it recycles the impure fluid via line 160 to pump 162 and thence via line 164 back into marker/stripper 150. If the tester 158 determines that the body fluid is adequately purified, it is fed via lines 50/52 back into the organism (see FIG. 4).

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A flow cytometer comprising means for sampling cellular material within a body comprised of blood, means for marking cells within said blood with a dye to produce marked cells, an analyzer for analyzing said marked cells, a dye stripper for removing said dye from said marked cells, a cell sorter for sorting said cells within said blood to produce sorted cells, and a reservoir comprising a permeable membrane for maintaining a first fraction of said sorted cells in a viable state.

2. The flow cytometer as recited in claim 1, further comprising means for removing said first fraction from said reservoir.

3. The flow cytometer as recited in claim 1, comprising means for returning said first fraction to said body.

* * * * *